United States Patent
Mäntyjärvi et al.

(10) Patent No.: US 6,983,219 B2
(45) Date of Patent: Jan. 3, 2006

(54) METHOD AND ARRANGEMENT FOR DETERMINING MOVEMENT

(75) Inventors: Jani Mäntyjärvi, Kempele (FI); Panu Korpipää, Oulu (FI)

(73) Assignee: Nokia Corporation, Espoo (FI)

(*) Notice: Subject to any disclaimer, the term of this patent is extended or adjusted under 35 U.S.C. 154(b) by 338 days.

(21) Appl. No.: 10/186,257

(22) Filed: Jun. 27, 2002

(65) Prior Publication Data

US 2003/0109258 A1 Jun. 12, 2003

(30) Foreign Application Priority Data

Jun. 29, 2001 (FI) .............................. 20011408

(51) Int. Cl.
   *G01C 19/00* (2006.01)
(52) U.S. Cl. ..................................... 702/153
(58) Field of Classification Search ............ 702/94–96, 702/141, 142, 150–154; 73/488, 492, 493
   See application file for complete search history.

(56) References Cited

U.S. PATENT DOCUMENTS

| | | | |
|---|---|---|---|
| 6,084,577 A | 7/2000 | Sato et al. | 345/179 |
| 6,122,960 A | 9/2000 | Hutchings et al. | 73/493 |

FOREIGN PATENT DOCUMENTS

| | | |
|---|---|---|
| EP | 0 816 986 A2 | 1/1998 |
| EP | 1 104 143 A2 | 5/2001 |

*Primary Examiner*—Michael Nghiem
(74) *Attorney, Agent, or Firm*—Hollingsworth & Funk, LLC (57) ABSTRACT

To determine the movement of a device, a three-dimensional measurement of the device's acceleration is provided in known directions with regard to the device, and average signals of acceleration signals parallel to different axes are formed to allow tilt angles of the device with respect to gravity to be defined. Acceleration change signals are formed by removing the average signals from their respective acceleration signals parallel to the different axes. The acceleration change signals and the tilt angles of the device are used for forming a component of the acceleration change of the device, which component is parallel to gravity and independent of the position of the device.

24 Claims, 7 Drawing Sheets

METHOD AND ARRANGEMENT FOR DETERMINING MOVEMENT

FIELD OF THE INVENTION

The invention relates to a solution for determining the movement of a device.

BACKGROUND OF THE INVENTION

Portable electronic devices are being used for increasingly diversified purposes. Typical examples of these devices are mobile phones and computers. The devices carry large amounts of data about the user, and they provide the user with access to various information channels. However, up to the present, the state associated with the movement of the device, or changes in the state, have not been utilized to any larger extent, although they would allow to recognize the user's activity context, which depends on the user's activities related to work or spare time, such as negotiations, travel or leisure activities.

One way of measuring the movement of a mobile device or to determine the user's activity context is to use one or more accelerometers to measure the accelerations of the device in one or more directions. Accelerations parallel to different dimensions vary according to activity context and they are characteristic of each activity context. In principle, it is therefore possible to identify activity contexts on the basis of the acceleration or movement data parallel to the different dimensions. For example, it is possible to try to identify whether the user is walking, running, walking up the stairs, etc. However, a problem involved in this is that the accelerometer signals change when the position of the device changes and therefore it is not possible to know the structural directions of the device to which the accelerations are really acting on. For example, it is not possible to measure the direction of gravity in relation to the axes parallel to the device's structures and, therefore, measurements cannot be used for determining whether the device is in an even approximately correct position, or upside down.

An attempt to solve this problem has been to attach the device always in the same position to the user. This does not, however, solve the problem, but complicates the use of the device. In addition, changes in the user's pose affect the position of the device and thereby change the directions of the accelerations, which makes it more difficult to recognise the direction of gravity in relation to the device.

SUMMARY OF THE INVENTION

It is an object of the invention to provide an improved method and an arrangement implementing the method to determine a dynamic acceleration component parallel with gravity and independent of the position of a device. This is achieved by a method for determining the movement of the device, in which method the acceleration of the device is measured at least in three different directions to provide a three-dimensional measurement. The method also comprises the steps of generating acceleration signals parallel to three orthogonal axes, which are in a known orientation to the device; generating average signals of the acceleration signals parallel to the different axes; defining tilt angles of the device in relation to the direction of gravity by means of the average signals; generating acceleration change signals by removing the average signals from their respective acceleration signals parallel to the different axes; forming a component of the acceleration change of the device by means of the acceleration change signals and the tilt angles of the device, which component is parallel to gravity and independent of the position of the device.

The invention also relates to an arrangement for determining the movement of a device, the arrangement being arranged to measure the acceleration of the device at least in three different directions to provide a three-dimensional measurement. The arrangement is arranged to measure acceleration signals in the direction of three orthogonal axes which are in a known orientation to the device; generate average signals of the acceleration signals parallel to the different axes; use the average signals for forming tilt angles of the device in relation to the direction of gravity; generate acceleration change signals by removing the average signals from their respective acceleration signals parallel to the different axes; form a component of the acceleration change of the device by means of the acceleration change signals and the tilt angles of the device, which component is parallel to gravity and independent of the position of the device.

The preferred embodiments of the invention are disclosed in the dependent claims.

The underlying idea of the invention is to measure device accelerations parallel to three dimensions and to use slowly changing accelerations for determining tilt angles of the device in relation to the direction of gravity. By removing slowly changing accelerations from total accelerations, rapidly changing accelerations are obtained. The device's rapidly changing accelerations and tilt angles are used for determining rapid acceleration changes parallel to gravity.

The method and arrangement of the invention provide several advantages. They allow acceleration parallel to gravity and changes in the acceleration to be determined irrespective of the position of the device, which is important when an activity context is to be identified.

BRIEF DESCRIPTION OF THE DRAWINGS

In the following, the invention will be described in greater detail in connection with preferred embodiments and with reference to the accompanying drawings, in which.

DETAILED DESCRIPTION OF THE INVENTION

The described solution is applicable in, although not restricted to, portable electronic user devices, such as mobile phones and computers.

Let us first examine some aspects relating to the activity context of a portable user device. When carried by the user, the position of a portable device usually varies according to situation, time and place (a mobile phone may be upside down in the pocket, attached to the belt in a horizontal position, or slightly tilted when held in hand). Changes in the position of the device in turn cause changes in signals measured in the directions of the device's different dimensions, thus making the position of the device and its activity context very difficult to recognize. In fact, the most important prerequisite for activity context recognition is that the position of the device is determined at least in the vertical direction. Additionally, the position should be determined in horizontal directions as well.

Figure 1:
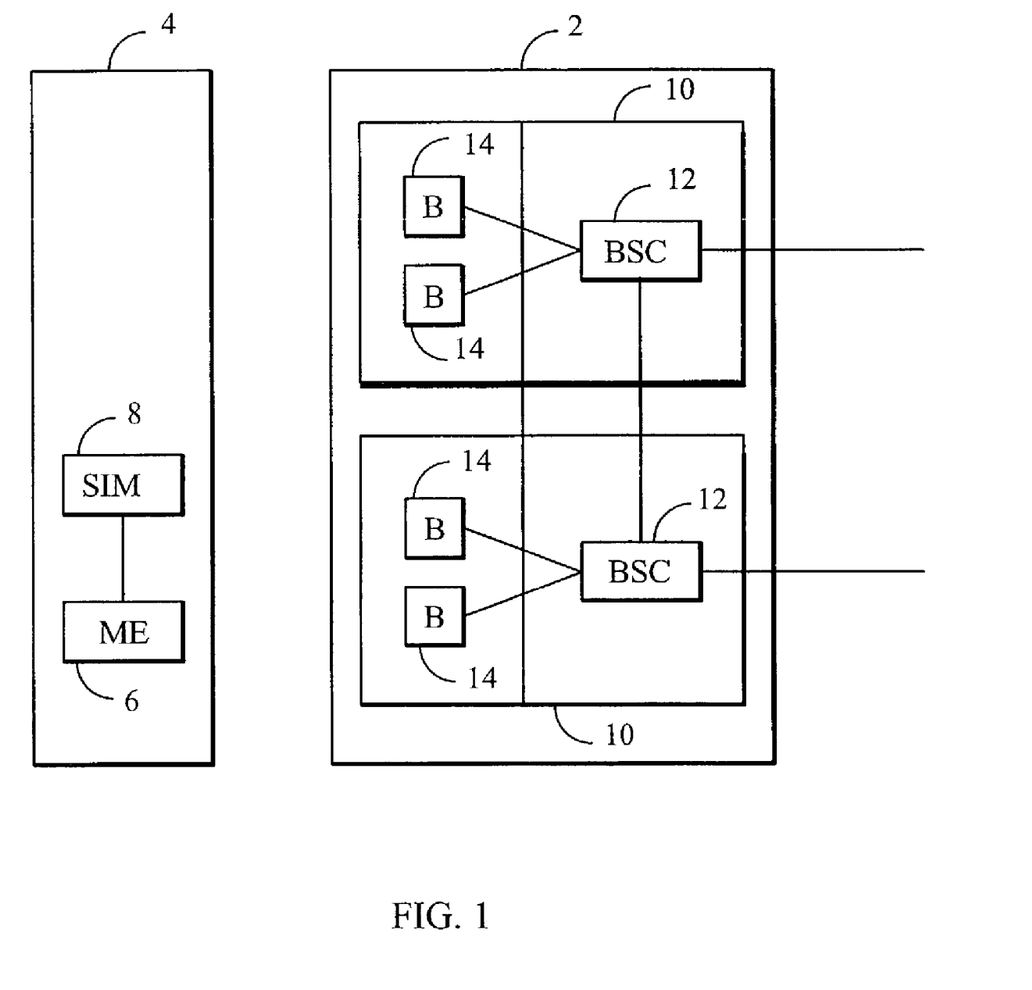
FIG. 1 illustrates the structure of a mobile phone system.

Before going into the described solution in detail, let us examine an example of a radio system structure with reference to FIG. 1, because one application of the described solution is to use it in portable devices connected to a radio system. The radio system may be for example a GSM or UMTS radio system and it comprises a terrestrial radio access network 2 and user equipment UE 4. The user equipment 4 comprises two parts: a functional unit which is mobile equipment ME 6, the radio terminal of which is used for setting up a radio link to the network 2, and a user-specific module, i.e. a subscriber identity module SIM 8, which is a smart card comprising user identity data and which typically executes identification algorithms and stores encryption parameters and subscriber data.

The network 2 is composed of radio network subsystems RNS 10 comprising base station controllers 12 and one or more base stations 14. Each base station controller 12 controls radio resources through the base stations connected to it.

Figure 2:
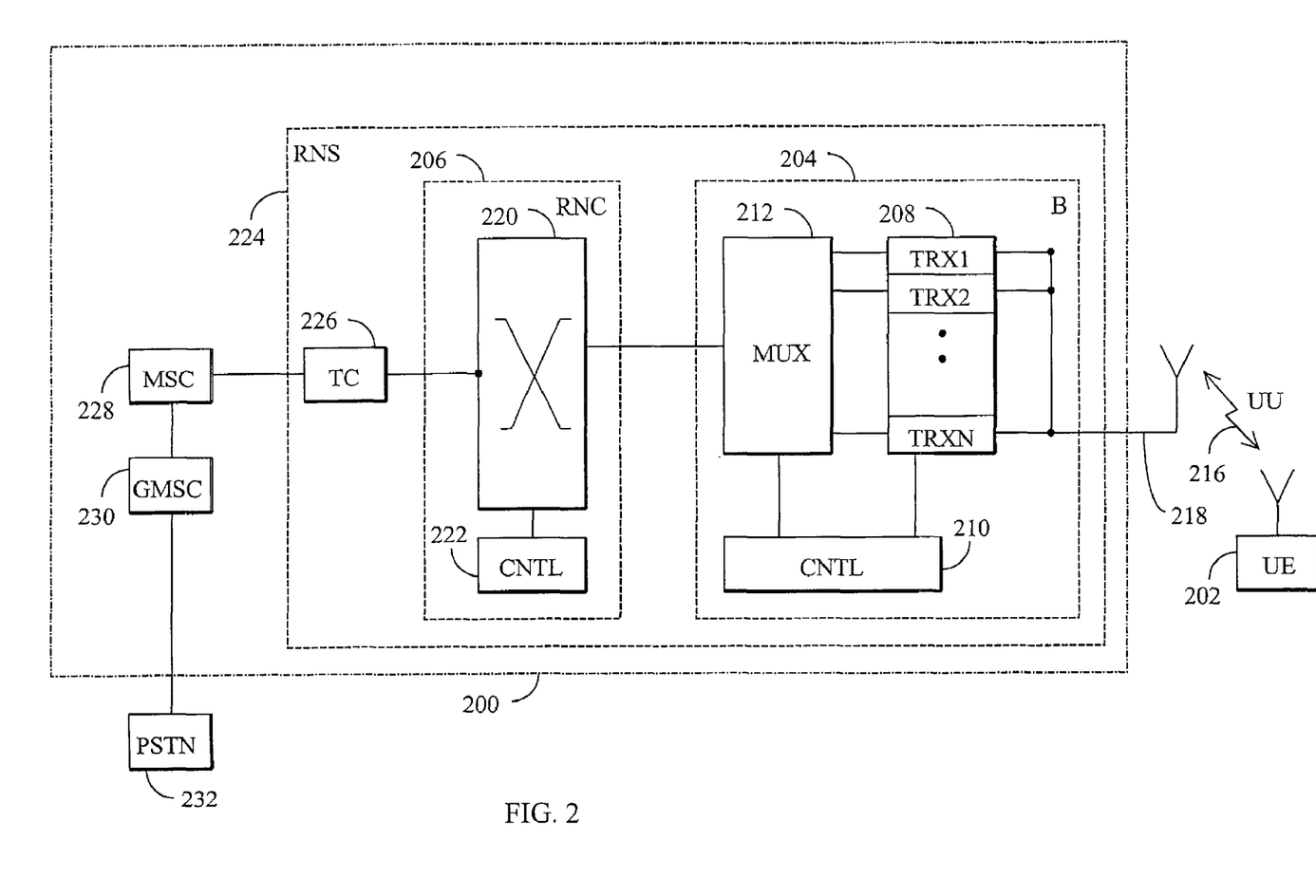
FIG. 2 illustrates a cellular radio system.

Since the illustration in FIG. 1 is fairly general, it is clarified by a more detailed example of a cellular radio system shown in FIG. 2. FIG. 2 only comprises the most essential blocks, but a person skilled in the art will find it apparent that a conventional cellular radio network also comprises other functions and structures, which need not be described in greater detail in this context. It should also be noted that the structure shown in FIG. 2 provides only one example.

The cellular radio network thus typically comprises a fixed network infrastructure, i.e. a network part 200, and user equipment 202, such as fixedly mounted, vehicle-mounted or handheld terminals. The network part 200 comprises base stations 204. A plural number of base stations 204 are in turn centrally controlled by a radio network controller 206 communicating with the base stations. A base station 204 comprises transceivers 208 and a multiplexer 212.

The base station 204 further comprises a control unit 210 which controls the operation of the transceivers 208 and the multiplexer 212. The multiplexer is used for arranging the traffic and control channels used by a plural number of transceivers 208 on one transmission link 214.

From the transceivers 208 of the base station 204 there is a connection to an antenna unit 218 which provides a bi-directional radio link 216 to the user equipment 202. The structure of the frames transferred on the bi-directional radio link 216 is defined for each system separately. In the preferred embodiments of the invention, at least a part of a signal is transmitted using three or more transmit antennas or three or more beams provided by a plural number of transmit antennas.

The radio network controller 206 comprises a group switching field 220 and a control unit 222. The group switching field 220 is used for switching speech and data and for connecting signalling circuits. The radio network subsystem 224 formed of the base station 204 and the radio network controller 206 further comprises a transcoder 226. The transcoder 226 is usually located as close to a mobile services switching centre 228 as possible, because speech can then be transferred between the transcoder 226 and the radio network controller 206 in a cellular radio network form, which saves transmission capacity.

The transcoder 226 converts different digital speech coding formats used between the public switched telephone network and the radio telephone network to make them compatible, for example from a fixed network format to another format in the cellular network, and vice versa. The control unit 222 carries out call control, mobility management, collection of statistical data and signalling.

FIG. 2 further illustrates the mobile services switching centre 228 and a gateway mobile services switching centre 230 which is responsible for the external connections of the mobile communications system, in this case for those to a public switched telephone network 232.

Figure 3:
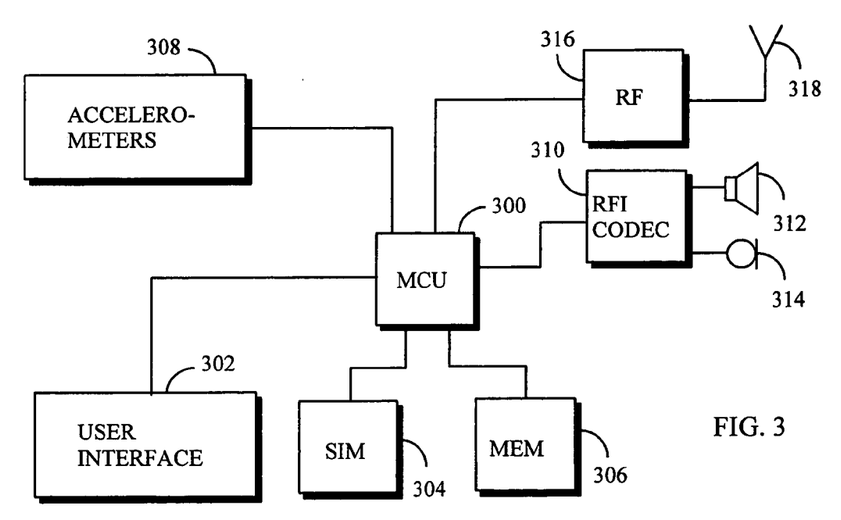
FIG. 3 is a block diagram illustrating a mobile phone.

With reference to FIG. 3, let us then examine an example of a portable user terminal in a GSM or UMTS radio system. The terminal comprises a processor 300 in which the software routines of the terminal are executed. The processor 300 is responsible for digital signal processing, for example, and it controls the operation of the other blocks. The terminal display and its keypad 302 serve as the user interface and they are used for displaying to the user visual information, such as text and images, processed by the processor 300, the user interface also allowing the user to produce such information. The processor 300 also carries out the checking of the SIM module 304. Information needed by the processor 300, such as the data needed for accelerometer calibration, is stored in a memory 306. An accelerometer block 308 comprises one or more accelerometers measuring acceleration in at least three orthogonal directions. Even in the case of only one accelerometer, it must be provided with elements that enable three-dimensional acceleration measurement. Acceleration signals provided by the accelerometers are supplied to the processor 300, which carries out the actual signal processing. A codec block 310 converts a signal coming from the processor 300 into a format suitable for a speaker 312 and the codec block 310 converts a signal coming from a microphone 314 to a format suitable for the processor 300. An RF block 316 in turn converts the digital signal to be transmitted which is received from the processor 300 to an analog radio frequency signal to allow it to be transmitted in the form of electromagnetic radiation over the antenna 318. Correspondingly, the radio frequency signal received by the antenna 318 is converted to lower frequency and digitized in the RF block 316 before the signal is supplied to the processor 300.

Acceleration is measured using one or more accelerometers which generate an electric signal corresponding to the acceleration to their output poles. The accelerometer may be electromechanical, for example. Its operation may be based on a piezoelectric crystal, for example, in which a change in the charge distribution is proportional to a force acting on the crystal.

Figure 4A:
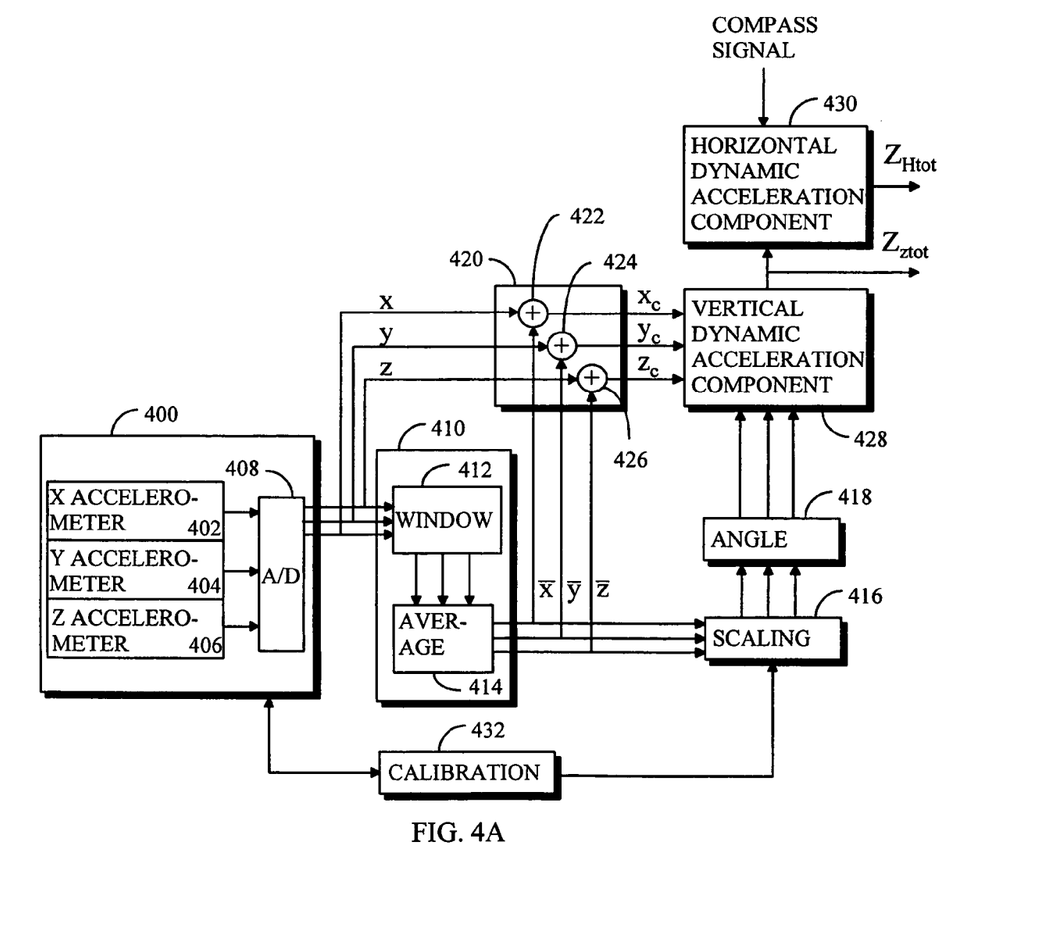
FIG. 4A is a block diagram of the described arrangement.
Figure 4B:
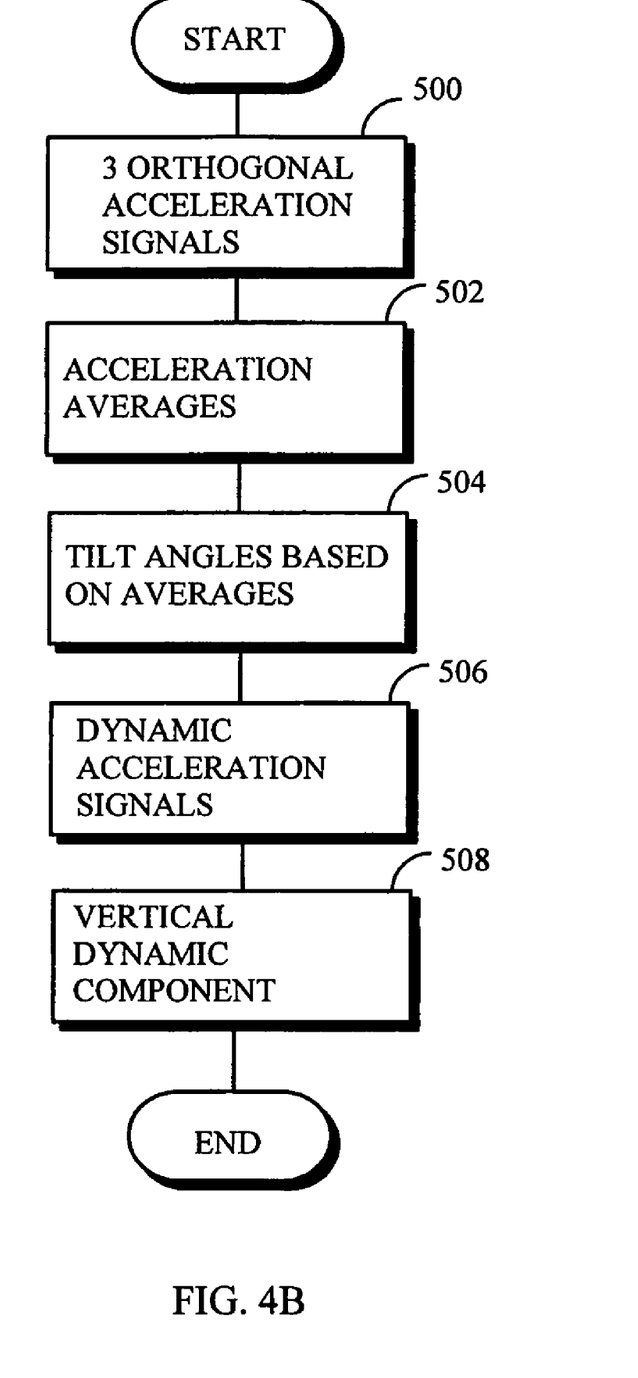
FIG. 4B is a flow diagram of the described arrangement.

Let us then examine the disclosed solution with reference to FIGS. 4A and 4B. FIG. 4A is a block diagram illustrating the described solution, and FIG. 4B is a flow diagram of the method. An accelerometer block 400 comprises at least three accelerometers 402, 404 and 406 which measure acceleration in the direction of three mutually orthogonal dimensions. The number of accelerometers may be more than three; what is essential is that the measurement signals of the accelerometers can be used for forming acceleration signals parallel with all the three dimensions as denoted in block 500. This structural solution is apparent to a person skilled in the art and therefore it will not be described in greater detail herein. The axes parallel to the measured dimensions are denoted with letters X, Y and Z, and they are preferably either identical with the structural directions $X_d$, $Y_d$ and $Z_d$ of the device, or at least in a known relation to them. In other words, the axes X, Y and Z represent the directions of the measurement axes, the directions $X_d$, $Y_d$ and $Z_d$ of the device's structural axes being parallel with the faces, or sides, of the device's cover or frame, or the like (the devices usually resemble a rectangular prism). The directions of the device's structural axes and the measurement directions are in a predetermined relation to each other, the dependencies between the measurement directions and the device's structural dimensions being expressed as $\theta=\theta_1+\Delta\theta$, $\phi=\phi_1+\Delta\phi$ and $\gamma=\gamma_1+\Delta\gamma$, where $\theta$ is the angle between the device's structural direction $X_d$ and gravity direction g, $\phi$ is the angle between the device's structural direction $Y_d$ and gravity direction g, $\gamma$ is the angle between the device's structural direction $Z_d$ and gravity direction g, and tilt angles $\theta$, $\phi$, $\gamma$ are within $\theta$, $\phi$, $\gamma$, $\in [-\pi/2, \pi/2]$.

The directions to be measured are preferably selected to relate to the structural directions of the electronic device, for example such that when the electronic device is in a vertical position with the display towards the user (who sees the letters in their correct position), the $Z_d$ axis points upward, the $Y_d$ axis points horizontally from left to right, and the $X_d$ axis points horizontally from front to back, directly to the user. The directions of the measured dimensions are thus preferably the same as the structural directions of the device, i.e. $X=X_d$, $Y=Y_d$ and $Z=Z_d$.

Figure 5A:
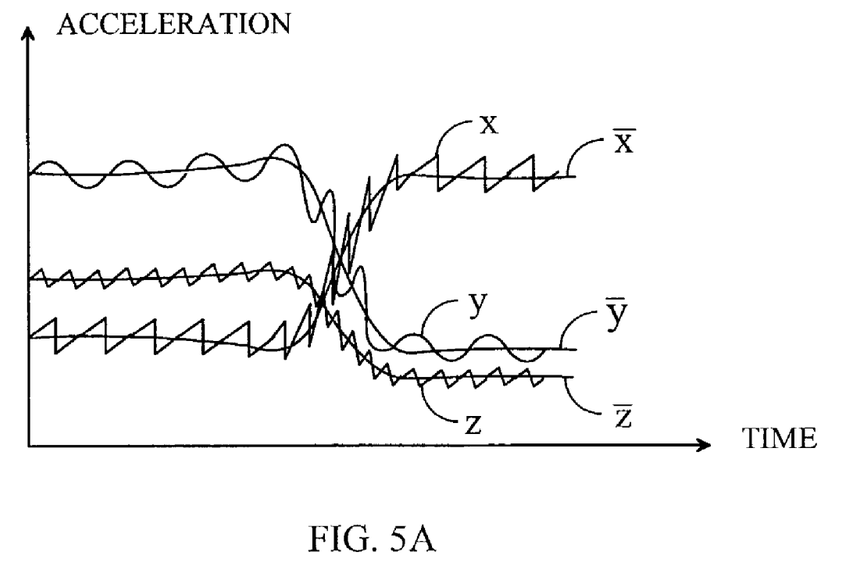
FIG. 5A shows slowly changing and rapidly changing accelerations parallel to three different dimensions.

Analog measurement signals parallel to the different dimensions are digitized in an A/D converter 408. The filtering of the digital acceleration signals is shown in blocks 410 and 502. It is carried out on the time plane by multiplying a signal sample sequence of a finite length by a window 412 of a finite length and a suitable frequency content, such as a Hanning window, which is suitable for separating dynamic signals from static ones. In addition, the average of multiple windowed signals is calculated in block 414. Instead of calculating the actual average, the averaging can be carried out using mean value calculation, low-pass filtering or other known methods. On the basis of the average, a static acceleration signal is formed, which hardly ever changes or which only reacts to slow changes. How slow phenomena should be taken into account can be freely selected for example by means of the window used for calculating the average. The average is calculated using a desired time window which can be formed for example as a Hanning window, known per se, in block 412. The Hanning windows for accelerations parallel to the different dimensions take the following mathematical forms:

$$x_i^w = \frac{1}{2}x_i\left[1-\cos\left(\frac{2\pi i}{n}\right)\right], \quad (1)$$

$$y_i^w = \frac{1}{2}y_i\left[1-\cos\left(\frac{2\pi i}{n}\right)\right] \text{ and}$$

$$z_i^w = \frac{1}{2}z_i\left[1-\cos\left(\frac{2\pi i}{n}\right)\right],$$

where $x_i$, $y_i$ and $z_i$ are acceleration samples parallel to the different dimensions; n is the number of samples in the window, $x_i^w$, $y_i^w$ ja $z_i^w$ are modified samples. Other possible windows known per se include the Hamming, Kaiser, Bessel and triangle windows. The average can be calculated in block 414 by applying for example formula (2):

$$\bar{x} = \frac{1}{n}\sum_{i=1}^{n} x_i^w, \bar{y} = \frac{1}{n}\sum_{i=1}^{n} y_i^w \text{ ja } \bar{z} = \frac{1}{n}\sum_{i=1}^{n} z_i^w, \quad (2)$$

where $\bar{x}$, $\bar{y}$ and $\bar{z}$ represent the averages. FIG. 5A shows the different acceleration signals x, y and z, and the averaged acceleration signals $\bar{x}$, $\bar{y}$ and $\bar{z}$. As shown in FIG. 5A, the averaged signals $\bar{x}$, $\bar{y}$ and $\bar{z}$ are in a way static DC signals of the measured acceleration signals. It is not necessary to form the averages $\bar{x}$, $\bar{y}$ and $\bar{z}$ from the windowed samples $x_i^w$, $y_i^w$ ja $z_i^w$, but the averages $\bar{x}$, $\bar{y}$ and $\bar{z}$ can also be calculated directly from the samples $x_i$, $y_i$ and $z_i$.

The averaged signals propagate further to a scaling block 416 where the levels of the filtered signals are arranged to be proportional to each other such that they may be used as sine function arguments. Since the averaged signals are in some cases directly applicable as sine function arguments, the scaling block 416 is not absolutely necessary in the disclosed solution. Scaling is used for example for rectifying distortions, if any, in the accelerometer operation. Manufacturers usually include the operations to be carried out in the scaling block in the accelerometers they deliver. Scaling thus ensures that averaged acceleration cannot exceed gravity acceleration, at least not on a continuous basis, and therefore the ratio of the accelerations measured in the different dimensions to the gravity acceleration corresponds to the ratio of a sine function of a tilt angle to the direction of gravity, i.e. $\bar{x}/g= \sin(\theta_1)$, $\bar{y}/g=\sin(\phi_1)$ and $\bar{z}/g=\sin(\gamma_1)$, where $\theta_1$ corresponds to the angle between measured acceleration direction X and gravity direction g, $\phi_1$ corresponds to the angle between measured acceleration direction Y and gravity direction g, and $\gamma_1$ corresponds to the angle between measured acceleration direction Z and gravity direction g. On the basis of angles $\theta_1$, $\phi_1$ and $\gamma_1$, tilt angles $\theta$, $\phi$ and $\gamma$ between the device's structural directions and gravity direction can be formed, because the directions of the structural axes of the device and the directions of the measurement are known to be proportional to each other.

In block 418 the accelerations parallel to the different dimensions and measured by the accelerometers are used to form tilt angles $\theta$, $\phi$ and $\gamma$ which illustrate the deviation of the different structural directions of the device from the gravity direction. This is also shown in block 504. If the structural directions of the device are the same as the directions of the measured accelerations, $\Delta\theta=\Delta\phi=\Delta\gamma=0$, and the angles can be formed as reverse sien functions $\theta_1=\theta=\arcsin(x/g)$, $\phi_1=\phi=\arcsin(y/g)$ and $\gamma_1=\gamma=\arcsin(z/g)$. Otherwise the deviation of the structural directions $X_d$, $Y_d$ and $Z_d$ from the measured directions X, Y and Z must be taken into account by calculating $\theta=\theta_1+\Delta\theta$, $\phi=\phi_1+\Delta\phi$ and $\gamma=\gamma_1+\Delta\gamma$.

Figure 5B:
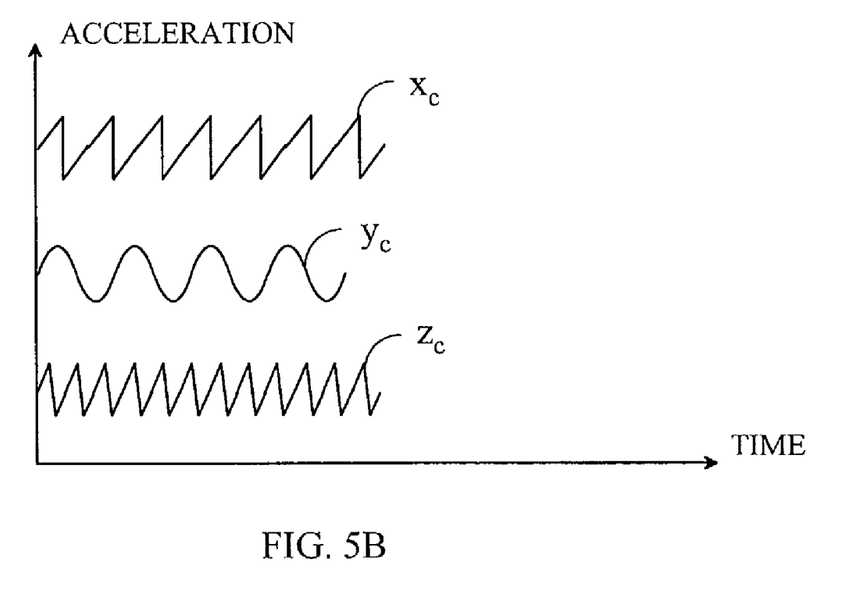
FIG. 5B shows rapidly changing accelerations parallel to three different dimensions.

In block 420, the averaged accelerations $\bar{x}$, $\bar{y}$ and $\bar{z}$ are subtracted from the measured accelerations x, y and z parallel to the different dimensions in sequences equal to the sample windows in length, whereby change signals $x_c$, $y_c$ and $z_c$ representing a continuous change in the accelerations are formed. This is shown in block 506. These acceleration change signals $x_c$, $y_c$ and $z_c$ represent rapid acceleration changes which are often regular as well, and which relate to the user's activity context, for example. FIG. 5B shows the acceleration change signals $x_c$, $y_c$ and $z_c$ parallel to the different directions of the device's structural axes as a function of time on a freely selected scale. The state of movement of the device may vary quite considerably in the different directions of the axes. As is shown in FIGS. 5A and 5B, the acceleration change signals are in a way dynamic AC signals of the measured acceleration signals. The subtraction is carried out for each dimension separately in sum blocks 422, 424 and 426 in which negations $-\bar{x}$, $-\bar{y}$ and $-\bar{z}$ of the averaged accelerations are added to the accelerations x, y and z.

In accordance with block 508, the acceleration change signals and the tilt angles $\theta$, $\phi$ and $\gamma$ of the device can be used in block 428 for forming a component $Z_{ztot}$ of the acceleration change of the device, the component being parallel to the earth's gravity acceleration and indicating continuously changing vertical accelerations parallel with gravity that act on the device. An essential aspect here is that in the vertical direction, the acceleration change component $Z_{ztot}$ of the device can be determined irrespective of the device's position. Vertical acceleration change sub-components of $X_z$, $Y_z$ and $Z_z$ are formed by multiplying the acceleration change signals $x_c$, $y_c$ and $z_c$ by sine functions of the device's tilt angles $\theta$, $\phi$ and $\gamma$ according to the following projections:

when $\text{sgn}(\theta)\geq 0$, $\text{sgn}(\phi)\geq 0$ and $\text{sgn}(\gamma)\geq 0$ $X_z=-x_c \sin(\theta)$ $Y_z=-y_c \sin(\phi)$ $Z_z=-z_c \sin(\gamma)$ and when $\text{sgn}(\theta)<0$, $\text{sgn}(\phi)<0$ and $\text{sgn}(\gamma)<0$ $X_z=x_c \sin|\theta|$ $Y_z=y_c \sin|\phi|$ $Z_z=z_c \sin|\gamma|$, (3)

where sgn( ) denotes a sign function whether the angle is positive or negative), and $|\theta|$, $|\phi|$ and $|\gamma|$ denote the absolute value of the angles $\theta$, $\phi$ and $\gamma$. The acceleration change component $Z_{ztot}$ parallel to gravity is the sum of the sub-components of acceleration change of the device: $Z_{ztot}=X_z+Y_z+Z_z$.

With reference to FIGS. 6A to 6H, let us now examine an alternative way of forming for the device an acceleration change component parallel to the earth's gravity. In this embodiment, the space depicted as a cube in FIGS. 6A to 6H is divided into eight parts relative to the corners of the cube. The direction of gravity with respect to each one of the three axes X, Y, Z may obtain two values $\pi/4\pm\pi/4$ or $-(\pi/4\pm\pi/4)$ and thus the number of parts is $2^3=8$. In this embodiment, the direction of a gravity vector is first determined on the basis of the signs of tilt angles $\theta$, $\phi$ and $\gamma$. When the signs have been determined, the appropriate calculation formula is selected. This procedure is entirely equivalent with formulae (3).

Figure 6A:
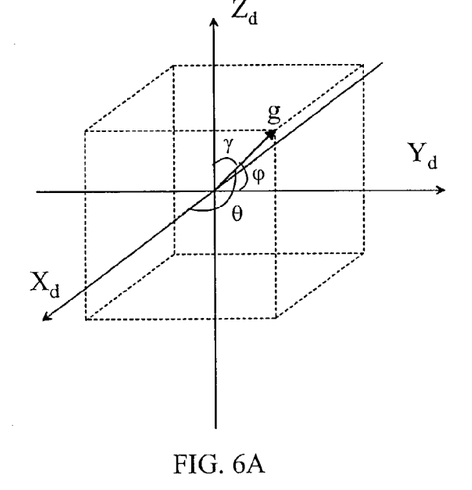
FIG. 6A shows gravity acting in a direction towards the upper right-hand front corner of a space defined on the basis of the structural axes of the device.

In FIG. 6A, gravity direction g is acting in the direction of the upper right-hand front corner of the cube, and for tilt angles $\theta$ and $\phi$ it is thus valid that $\text{sgn}(\theta)<0$, $\text{sgn}(\phi)<0$. In addition, angle $\gamma$ is defined as $\text{sgn}(\gamma)\geq 0$. This provides the following calculation formulae ⅛ for the acceleration change components in the vertical direction:

$X_z=x_c \sin|\theta|$ $Y_z=y_c \sin|\phi|$ $Z_z=-z_c \sin(\gamma)$.

Figure 6B:
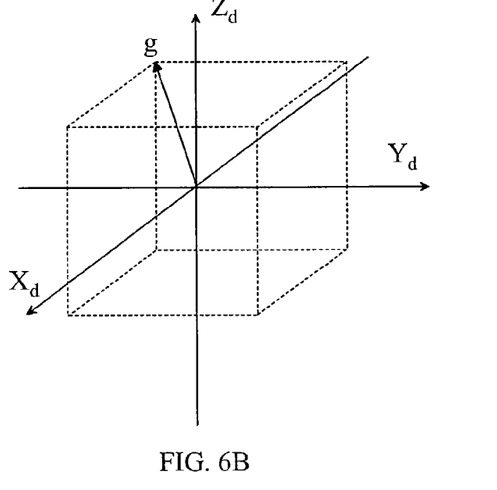
FIG. 6B shows gravity acting in a direction towards the upper left-hand rear corner of a space defined on the basis of the structural axes of the device.

In FIG. 6B, the gravity vector points to the upper left-hand rear corner of the cube, and for tilt angles $\theta$, $\phi$ and $\gamma$ it is thus valid that $\text{sgn}(\theta)\geq 0$, $\text{sgn}(\phi)\geq 0$ and $\text{sgn}(\gamma)\geq 0$. This provides the following calculation formulae ⅜ for the acceleration change components in the vertical direction:

$X_z=-x_c \sin(\theta)$ $Y_z=-y_c \sin(\phi)$ $Z_z=-z_c \sin(\gamma)$

Figure 6C:
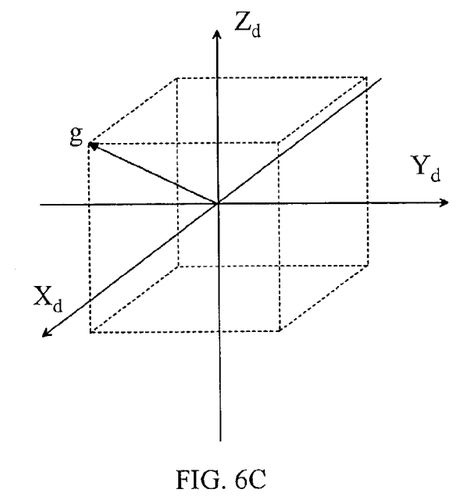
FIG. 6C shows gravity acting in a direction towards the upper left-hand front corner of a space defined on the basis of the structural axes of the device.

In FIG. 6C gravity direction g is acting in the direction of the upper left-hand front corner of the cube, and for tilt angles $\theta$, $\phi$ and $\gamma$ it is thus valid that $\text{sgn}(\theta)<0$, $\text{sgn}(\phi)\geq 0$ and $\text{sgn}(\gamma)\geq 0$. This provides the following calculation formulae ⅜ for the acceleration change components in the vertical direction:

$X_z=x_c \sin|\theta|$ $Y_z=-y_c \sin(\phi)$ $Z_z=-z_c \sin(\gamma)$.

Figure 6D:
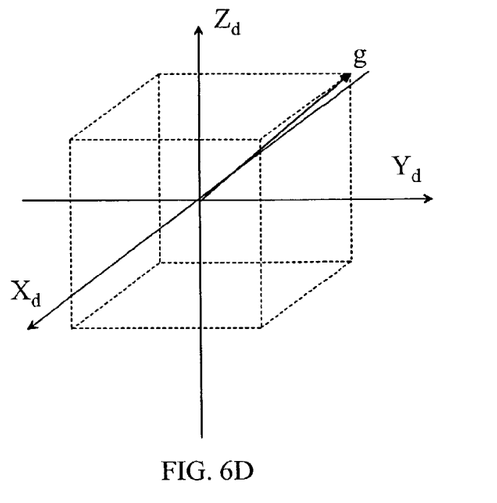
FIG. 6D shows gravity acting in a direction towards the upper right-hand rear corner of a space defined on the basis of the structural axes of the device.

In FIG. 6D gravity direction g is acting in the direction of the upper right-hand rear corner of the cube, and for tilt angles $\theta$, $\phi$ and $\gamma$ it is thus valid that $\text{sgn}(\theta)\geq 0$, $\text{sgn}(\phi)<0$ and $\text{sgn}(\gamma)\geq 0$. This provides the following calculation formulae ⅛ for the acceleration change components in the vertical direction:

$X_z=-x_c \sin(\theta)$ $Y_z=y_c \sin|\phi|$ $Z_z=-z_c \sin(\gamma)$.

Figure 6E:
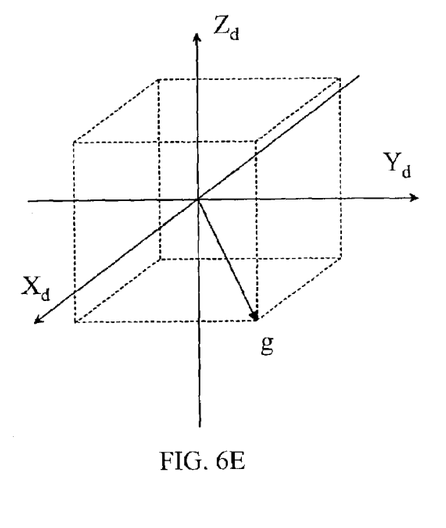
FIG. 6E shows gravity acting in a direction towards the lower right-hand front corner of a space defined on the basis of the structural axes of the device.

In FIG. 6E gravity direction g is acting in the direction of the lower right-hand front corner of the cube, and for tilt angles $\theta$, $\phi$ and $\gamma$ it is thus valid that $\text{sgn}(\theta)<0$, $\text{sgn}(\phi)<0$ and $\text{sgn}(\gamma)<0$. This provides the following calculation formulae ⅝ for the acceleration change components in the vertical direction:

$X_z=x_c \sin|\theta|$ $Y_z=y_c \sin|\phi|$ $Z_z=z_c \sin|\gamma|$.

Figure 6F:
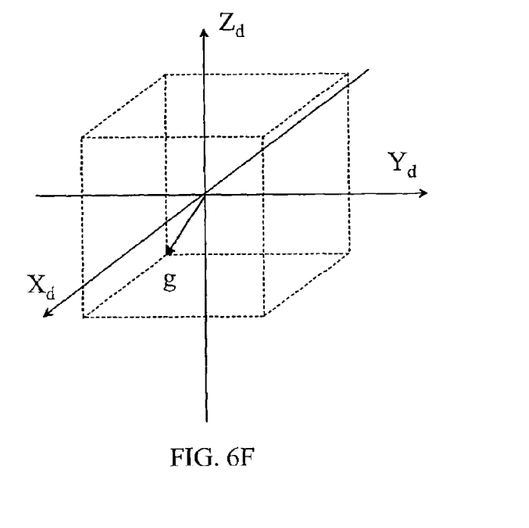
FIG. 6F shows gravity acting in a direction towards the lower left-hand rear corner of a space defined on the basis of the structural axes of the device.

In FIG. 6F gravity direction g is acting in the direction of the lower left-hand rear corner of the cube, and for tilt angles $\theta$, $\phi$ and $\gamma$ it is thus valid that $\text{sgn}(\theta)\geq 0$, $\text{sgn}(\phi)\geq 0$ and sgn(γ)<0. This provides the following calculation formulae ⁶/₈ for the acceleration change components in the vertical direction:

$$X_z = -x_c \sin(\theta)$$
$$Y_z = -y_c \sin(\phi)$$
$$Z_z = z_c \sin|\gamma|.$$

Figure 6G:
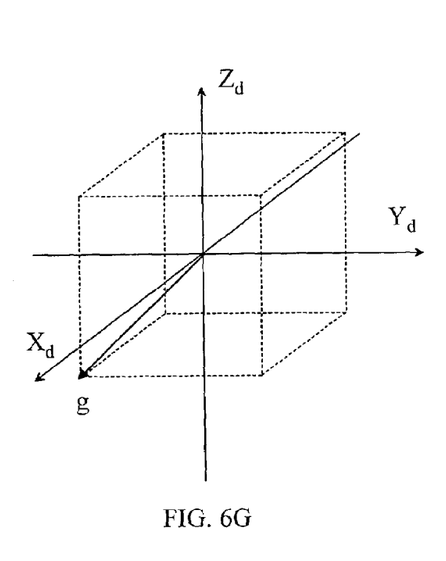
FIG. 6G shows gravity acting in a direction towards the lower left-hand front corner of a space defined on the basis of the structural axes of the device.

In FIG. 6G gravity direction g is acting in the direction of the lower left-hand front corner of the cube, and for tilt angles θ, φ and γ it is thus valid that sgn(θ)≧0, sgn(φ)<0 and sgn(γ)<0. This provides the following calculation formulae ⁷/₈ for the acceleration change components in the vertical direction:

$$X_z = x_c \sin|\theta|$$
$$Y_z = -y_c \sin(\phi)$$
$$Z_z = z_c \sin|\gamma|.$$

Figure 6H:
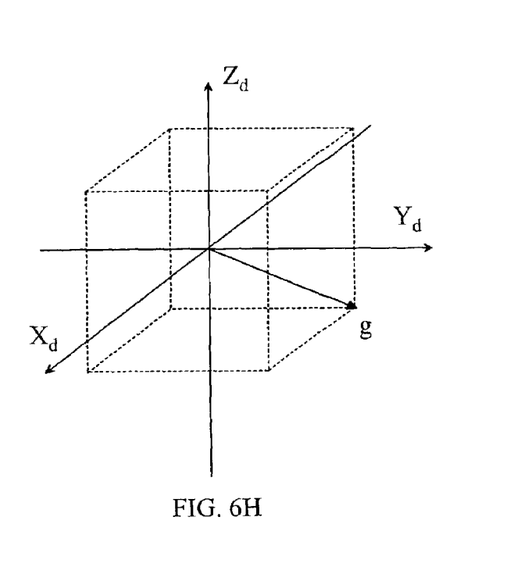
FIG. 6H shows gravity acting in a direction towards the lower right-hand rear corner of a space defined on the basis of the structural axes of the device.

Finally, in FIG. 6H gravity direction g is acting in the direction of the lower right-hand rear corner of the cube, and for tilt angles θ, φ and γ it is thus valid that sgn(θ)<0, sgn(φ)<0 and sgn(γ)<0. This provides the following calculation formulae ⁸/₈ for the acceleration change components in the vertical direction:

$$X_z = -x_c \sin(\theta)$$
$$Y_z = -y_c \sin(\phi)$$
$$Z_z = z_c \sin|\gamma|.$$

Also in this case the acceleration change component $Z_{ztot}$ parallel to gravity is the sum of the change components: $Z_{ztot} = X_z + Y_z + Z_z$.

In block 430 the vertical total acceleration $Z_{ztot}$ is removed from the change signals $x_c$, $y_c$ and $z_c$, whereby a horizontal acceleration change component $Z_{htot}$ is formed which represents changing accelerations acting on the device in horizontal directions. The mathematical form in which this is carried out is subtraction: $Z_{Htot} = (x_c + y_c + z_c) - Z_{ztot}$. However, this calculation does not allow the direction of the horizontal acceleration change component to be determined in greater detail.

The described solution may also employ a compass, which may be an ordinary compass based on a magnetic needle, or a gyrocompass. The compass is used for arranging a horizontal direction in relation to two orthogonal axes. This allows the position of the device with respect to earth's magnetic field to be accurately defined at the same time as acceleration information. A preferred way to select the horizontal axes is one in which a first axis $X_{ns}$ is in the north-south direction and a second axis $Y_{ew}$ is in the east-west direction. These axes allow the horizontal acceleration change component $Z_{htot}$ formed in block 430 to be determined by means of the horizontal sub-components $Z_{ns}$ and $Z_{ew}$ of change serving as projections of the axes.

In block 432 is stored accelerometer calibration values which are used for correcting non-linearities in the accelerometers. Examples of the calibration include crawling, temperature changes, the magnitude of gravity at the earth's different latitudes, and the like.

Although the invention is described above with reference to an example shown in the attached drawings, it is apparent that the invention is not restricted to it, but can vary in many ways within the inventive idea disclosed in the attached claims.

What is claimed is:

1. A method for determining the movement of a device, in which method the acceleration of the device is measured at least in three different directions to provide a three-dimensional measurement, the method comprising
    generating acceleration signals parallel to three orthogonal axes, which are in a known orientation to the device;
    generating average signals of the acceleration signals parallel to the different axes;
    defining tilt angles of the device in relation to the direction of gravity by means of the average signals;
    generating acceleration change signals by removing the average signals from their respective acceleration signals parallel to the different axes;
    forming a component of the acceleration change of the device by means of the acceleration change signals and the tilt angles of the device, which component is parallel to gravity and independent of the position of the device.

2. A method according to claim 1, further comprising forming a horizontal acceleration change component by removing the acceleration change component parallel to gravity from the acceleration change signals.

3. A method according to claim 1, wherein the orthogonal axes are in known orientations in relation to the structural directions of the device, and tilt angles of the structural directions of the device in relation to the direction of gravity are formed using the average signals.

4. A method according to claim 1, further comprising forming the acceleration change components $X_z$, $Y_z$ and $Z_z$ by multiplying the acceleration change signals $x_c$, $y_c$ and $z_c$ by the sine function of the device's tilt angles θ, φ and γ according to the following projections:

if sgn(θ)≧0, sgn(φ)≧0 and sgn(γ)≧0

$$X_z = -x_c \sin(\theta)$$
$$Y_z = -y_c \sin(\phi)$$
$$Z_z = -z_c \sin(\gamma), \text{ or}$$

if sgn(θ)<0, sgn(φ)<0 and sgn(γ)<0

$$X_z = x_c \sin|\theta|$$
$$Y_z = y_c \sin|\phi|$$
$$Z_z = z_c \sin|\gamma|,$$

where sgn( ) denotes a sign function, |θ|, |φ| and |γ| denote the absolute values of angles θ, φ and γ; and that an acceleration change signal $Z_{ztot}$ parallel to gravity is formed as the sum of the sub-components of acceleration change: $Z_{ztot} = X_z + Y_z + Z_z$.

5. A method according to claim 1, further comprising dividing the spatial directions defined by the axes into portions, separate formulae being determined for forming a vertical acceleration change component for each portion;
    determining the portion in the direction of which gravity acts using the tilt angles; and
    forming a vertical acceleration change component according to the device portion in question.

6. A method according to claim 5, further comprising dividing the spatial directions defined by the axes into eight portions such that the direction of gravity in relation to each one of the three measured axis directions obtains the values ($\pi/4\pm\pi/4$) or $-(\pi/4\pm\pi/4)$, separate formulae being determined for forming sub-components of vertical acceleration change for each portion, and if $sgn(\theta)<0$, $sgn(\phi)<0$ and $sgn(\gamma)\geq 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = y_c \sin|\phi|$ $Z_z = -z_c \sin(\gamma)$, if $sgn(\theta)\geq 0$, $sgn(\phi)\geq 0$ and $sgn(\gamma)\geq 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = -z_c \sin(\gamma)$ if $sgn(\theta)<0$, $sgn(\phi)\geq 0$ and $sgn(\gamma)\geq 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = -y_c \sin(\phi)$ $Z_z = -z_c \sin(\gamma)$ if $sgn(\theta)\geq 0$, $sgn(\phi)<0$ and $sgn(\gamma)\geq 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = y_c \sin|\phi|$ $Z_z = -z_c \sin(\gamma)$, if $sgn(\theta)<0$, $sgn(\phi)<0$ and $sgn(\gamma)<0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = y_c \sin|\phi|$ $Z_z = z_c \sin|\gamma|$, if $sgn(\theta)\geq 0$, $sgn(\phi)\geq 0$ and $sgn(\gamma)<0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = z_c \sin|\gamma|$, if $sgn(\theta)\geq 0$, $sgn(\phi)<0$ and $sgn(\gamma)<0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = -y_c \sin(\phi)$ $Z_z = z_c \sin|\gamma|$, and if $sgn(\theta)<0$, $sgn(\phi)<0$ and $sgn(\gamma)<0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = z_c \sin|\gamma|$; and the acceleration change component $Z_{ztot}$ of the device is formed parallel to gravity as a sum of the change components: $Z_{ztot} = X_z + Y_z + Z_z$.

7. A method according to claim 1, the method further comprising
forming a horizontal acceleration change component by removing the acceleration change component parallel to gravity from the acceleration change signals;
determining two mutually orthogonal directions in the horizontal plane by means of a compass; and
determining sub-components of acceleration change as projections of the horizontal acceleration change component parallel to the orthogonal axes.

8. A method according to claim 1, further comprising windowing, before the average signals are formed, the acceleration signals using a desired windowing function.

9. An arrangement for determining the movement of a device, the arrangement being arranged to measure the acceleration of the device at least in three different directions to provide a three-dimensional measurement, the arrangement comprising:
means for measuring acceleration signals parallel to three orthogonal axes, which are in a known orientation to the device;
means for generating average signals of the acceleration signals parallel to the different axes;
means for defining tilt angles of the device in relation to the direction of gravity by means of the average signals;
means for generating acceleration change signals by removing the average signals from their respective acceleration signals parallel to the different axes; and
means for forming a component of the acceleration change of the device by means of the acceleration change signals and the tilt angles of the device, which component is parallel to gravity and independent of the position of the device.

10. An arrangement according to claim 9, wherein the arrangement is arranged to form a horizontal acceleration change component by removing the acceleration change component parallel to gravity from the acceleration change signals.

11. An arrangement according to claim 9, wherein the orthogonal axes are in known orientations in relation to the structural directions of the device, and that the arrangement is arranged to form tilt angles of the structural directions of the device in relation to the direction of gravity by using the average signals.

12. An arrangement according to claim 9, wherein the arrangement is arranged to form the sub-components $X_z$, $Y_z$ and $Z_z$ of acceleration change by multiplying the acceleration change signals $x_c$, $y_c$ and $z_c$ by the sine function of the device's tilt angles $\theta$, $\phi$ and $\gamma$ according to the following projections:

if $sgn(\theta)\geq 0$, $sgn(\phi)\geq 0$ and $sgn(\gamma)\geq 0$ $X_z = -x_c \sin(\theta)$ $Y_z = -y_c \sin(\phi)$ $Z_z = -z_c \sin(\gamma)$, or if $\operatorname{sgn}(\theta) < 0$, $\operatorname{sgn}(\phi) < 0$ and $\operatorname{sgn}(\gamma) < 0$ $X_z = x_c \sin|\theta|$ $Y_z = y_c \sin|\phi|$ $Z_z = z_c \sin|\gamma|$, where sgn( ) denotes a sign function, $|\theta|$, $|\phi|$ and $|\gamma|$ denote the absolute values of angles $\theta$, $\phi$ and $\gamma$; and that the arrangement is arranged to form the acceleration change component $Z_{ztot}$ parallel to gravity as the sum of the sub-components of acceleration change: $Z_{ztot} = X_z + Y_z + Z_z$.

13. An arrangement according to claim 9, wherein the spatial directions defined by the axes are divided into portions, separate formulae being determined for forming a vertical acceleration change component for each portion;
   the arrangement is arranged to determine the portion in the direction of which gravity acts by using the tilt angles; and
   the arrangement is arranged to form the vertical acceleration change component according to the device portion in question.

14. An arrangement according to claim 13, wherein the spatial directions defined by the axes are divided into eight portions such that the direction of gravity in relation to each one of the three measured axis directions obtains the values $(\pi/4 \pm \pi/4)$ or $-(\pi/4 \pm \pi/4)$, separate formulae being defined for each portion for forming sub-components of vertical acceleration change; and
   if $\operatorname{sgn}(\theta) < 0$, $\operatorname{sgn}(\phi) < 0$ and $\operatorname{sgn}(\gamma) \geq 0$ are valid for tilt angles $\theta$, $\phi$ and $\gamma$, the arrangement is arranged to form the sub-components $X_z$, $Y_z$ and $Z_z$ of acceleration change as follows:

$X_z = x_c \sin|\theta|$ $Y_z = y_c \sin|\phi|$ $Z_z = -z_c \sin(\gamma)$, if $\operatorname{sgn}(\theta) \geq 0$, $\operatorname{sgn}(\phi) \geq 0$ and $\operatorname{sgn}(\gamma) \geq 0$ are valid for tilt angles $\theta$, $\phi$ and $\gamma$, the arrangement is arranged to form the sub-components $X_z$, $Y_z$ and $Z_z$ of acceleration change as follows:

$X_z = -x_c \sin(\theta)$ $Y_z = -y_c \sin(\phi)$ $Z_z = -z_c \sin(\gamma)$ if $\operatorname{sgn}(\theta) < 0$, $\operatorname{sgn}(\phi) \geq 0$ and $\operatorname{sgn}(\gamma) \geq 0$ are valid for tilt angles $\theta$, $\phi$ and $\gamma$, the arrangement is arranged to form sub-components $X_z$, $Y_z$ and $Z_z$ of acceleration change as follows:

$X_z = x_c \sin|\theta|$ $Y_z = -y_c \sin(\phi)$ $Z_z = -z_c \sin(\gamma)$, if $\operatorname{sgn}(\theta) \geq 0$, $\operatorname{sgn}(\phi) < 0$ and $\operatorname{sgn}(\gamma) \geq 0$ are valid for tilt angles $\theta$, $\phi$ and $\gamma$, the arrangement is arranged to form the sub-components $X_z$, $Y_z$ and $Z_z$ of acceleration change as follows:

$X_z = -x_c \sin(\theta)$ $Y_z = y_c \sin|\phi|$ $Z_z = -z_c \sin(\gamma)$, if $\operatorname{sgn}(\theta) < 0$, $\operatorname{sgn}(\phi) < 0$ and $\operatorname{sgn}(\gamma) \geq 0$ are valid for tilt angles $\theta$, $\phi$ and $\gamma$, the arrangement is arranged to form the sub-components $X_z$, $Y_z$ and $Z_z$ of acceleration change as follows:

$X_z = x_c \sin|\theta|$ $Y_z = y_c \sin|\phi|$ $Z_z = z_c \sin|\gamma|$, if $\operatorname{sgn}(\theta) \geq 0$, $\operatorname{sgn}(\phi) \geq 0$ and $\operatorname{sgn}(\gamma) < 0$ are valid for tilt angles $\theta$, $\phi$ and $\gamma$, the arrangement is arranged to form sub-components $X_z$, $Y_z$ and $Z_z$ of acceleration change as follows:

$X_z = -x_c \sin(\theta)$ $Y_z = -y_c \sin(\phi)$ $Z_z = -z_c \sin|\gamma|$, if $\operatorname{sgn}(\theta) \geq 0$, $\operatorname{sgn}(\phi) < 0$ and $\operatorname{sgn}(\gamma) < 0$ are valid for tilt angles $\theta$, $\phi$ and $\gamma$, the arrangement is arranged to form the sub-components $X_z$, $Y_z$ and $Z_z$ of acceleration change as follows:

$X_z = x_c \sin|\theta|$ $Y_z = -y_c \sin(\phi)$ $Z_z = z_c \sin|\gamma|$, and if $\operatorname{sgn}(\theta) < 0$, $\operatorname{sgn}(\phi) < 0$ and $\operatorname{sgn}(\gamma) < 0$ are valid for tilt angles $\theta$, $\phi$ and $\gamma$, the arrangement is arranged to form the sub-components $X_z$, $Y_z$ and $Z_z$ of acceleration change as follows:

$X_z = -x_c \sin(\theta)$ $Y_z = -y_c \sin(\phi)$ $Z_z = z_c \sin|\gamma|$; and the arrangement is arranged to form the acceleration change component $Z_{ztot}$ of the device parallel to gravity as the sum of the change components: $Z_{ztot} = X_z + Y_z + Z_z$.

15. An arrangement according to claim 9, wherein the arrangement is arranged to form a horizontal acceleration change component by removing the acceleration change component parallel to gravity from the acceleration change signals;
   the arrangement is arranged to determine two mutually orthogonal directions in the horizontal plane by means of a compass; and
   the arrangement is arranged to determine sub-components of acceleration change as projections of the horizontal acceleration change component parallel to the orthogonal axes.

16. An arrangement according to claim 9, wherein the arrangement is arranged to window the acceleration signals using a desired windowing function before the average signals are formed.

17. For determining the movement of a device by measuring acceleration of the device at least in three different directions to provide a three-dimensional measurement, a computer readable medium having computer-executable instructions for performing a method comprising:
   generating acceleration signals parallel to three orthogonal axes, which are in a known orientation to the device;
   generating average signals of the acceleration signals parallel to the different axes;
   defining tilt angles of the device in relation to the direction of gravity by means of the average signals;

generating acceleration change signals by removing the average signals from their respective acceleration signals parallel to the different axes; and forming a component of the acceleration change of the device by means of the acceleration change signals and the tilt angles of the device, which component is parallel to gravity and independent of the position of the device.

18. The computer readable medium according to claim 17, the method further comprising forming a horizontal acceleration change component by removing the acceleration change component parallel to gravity from the acceleration change signals.

19. The computer readable medium according to claim 17, the method further comprising forming tilt angles of the structural directions of the device in relation to the direction of gravity using the average signals when the orthogonal axes are in known orientations in relation to the structural directions of the device.

20. The computer readable medium according to claim 17, the method further comprising forming the acceleration change components $X_z$, $Y_z$ and $Z_z$ by multiplying the acceleration change signals $x_c$, $Y_c$ and $z_c$ by the sine function of the device's tilt angles $\theta$, $\phi$ and $\gamma$ according to the following projections:

if $\text{sgn}(\theta) \geq 0$, $\text{sgn}(\phi) \geq 0$ and $\text{sgn}(\gamma) \geq 0$ $X_z = -x_c \sin(\theta)$ $Y_z = -y_c \sin(\phi)$ $Z_z = -z_c \sin(\gamma)$, or if $\text{sgn}(\theta) < 0$, $\text{sgn}(\phi) < 0$ and $\text{sgn}(\gamma) < 0$ $X_z = x_c \sin|\theta|$ $Y_z = y_c \sin|\phi|$ $Z_z = z_c \sin|\gamma|$, where sgn() denotes a sign function, $|\theta|$, $|\phi|$ and $|\gamma|$ denote the absolute values of angles $\theta$, $\phi$ and $\gamma$; and that an acceleration change signal $Z_{ztot}$ parallel to gravity is formed as the sum of the sub-components of acceleration change: $Z_{ztot} = X_z + Y_z + Z_z$.

21. The computer readable medium according to claim 17, the method further comprising dividing the spatial directions defined by the axes into portions, separate formulae being determined for forming a vertical acceleration change component for each portion; determining the portion in the direction of which gravity acts using the tilt angles; and forming a vertical acceleration change component according to the device portion in question.

22. The computer readable medium according to claim 21, the method further comprising dividing the spatial directions defined by the axes into eight portions such that the direction of gravity in relation to each one of the three measured axis directions obtains the values $(\pi/4 \pm \pi/4)$ or $-(\pi/4 \pm \pi/4)$, separate formulae being determined for forming sub-components of vertical acceleration change for each portion, and if $\text{sgn}(\theta) < 0$, $\text{sgn}(\phi) < 0$ and $\text{sgn}(\gamma) \geq 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = y_c \sin|\phi|$ $Z_z = z_c \sin(\gamma)$, if $\text{sgn}(\theta) \geq 0$, $\text{sgn}(\phi) \geq 0$ and $\text{sgn}(\gamma) \geq 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = -z_c \sin(\gamma)$, if $\text{sgn}(\theta) < 0$, $\text{sgn}(\phi) \geq 0$ and $\text{sgn}(\gamma) \geq 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = -y_c \sin(\phi)$ $Z_z = -z_c \sin(\gamma)$, if $\text{sgn}(\theta) \geq 0$, $\text{sgn}(\phi) < 0$ and $\text{sgn}(\gamma) \geq 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = y_c \sin|\phi|$ $Z_z = -z_c \sin(\gamma)$, if $\text{sgn}(\theta) < 0$, $\text{sgn}(\phi) < 0$ and $\text{sgn}(\gamma) < 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = y_c \sin|\phi|$ $Z_z = z_c \sin|\gamma|$, if $\text{sgn}(\theta) \geq 0$, $\text{sgn}(\phi) \geq 0$ and $\text{sgn}(\gamma) < 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = z_c \sin|\gamma|$, if $\text{sgn}(\theta) \geq 0$, $\text{sgn}((\phi) < 0$ and $\text{sgn}(\gamma) < 0$ are valid for tilt angles $\theta$, $\phi$ and $\gamma$, the sub-components $X_z$, $Y_z$ and $Z_z$ of acceleration change are formed as follows:

$X_z = x_c \sin|\theta|$ $Y_z = -y_c \sin(\phi)$ $Z_z = z_c \sin|\gamma|$, and if $\text{sgn}(\theta) < 0$, $\text{sgn}(\phi) < 0$ and $\text{sgn}(\gamma) < 0$ are valid for tilt angles $\theta$, $\phi$ and $\gamma$, the sub-components $X_z$, $Y_z$ and $Z_z$ of acceleration change are formed as follows:

$X_z = -x_c \sin(\theta)$ $Y_z = -y_c \sin(\phi)$ $Z_z = z_c \sin|\gamma|$; and the acceleration change component $Z_{ztot}$ of the device is formed parallel to gravity as a sum of the change components: $Z_{ztot}=X_z+Y_z+Z_z$.

23. The computer readable medium according to claim 17, the method further comprising forming a horizontal acceleration change component by removing the acceleration change component parallel to gravity from the acceleration change signals; determining two mutually orthogonal directions in the horizontal plane by means of a compass; and determining sub-components of acceleration change as projections of the horizontal acceleration change component parallel to the orthogonal axes.

24. The computer readable medium according to claim 17, the method further comprising windowing, before the average signals are formed, the acceleration signals using a desired windowing function.

* * * * *

UNITED STATES PATENT AND TRADEMARK OFFICE
CERTIFICATE OF CORRECTION

PATENT NO. : 6,983,219 B2
APPLICATION NO. : 10/186257
DATED : January 3, 2006
INVENTOR(S) : Mäntyjärvi et al.

It is certified that error appears in the above-identified patent and that said Letters Patent is hereby corrected as shown below:

In the Specification

Col. 6, line 13: "where $x_i$, $y_1$ and $z_i$" should read -- where $x_i$, $y_i$, and $z_i$ --.

Col. 6, line 15: "where $x_i^w$, $y_i^w$ ja $z_i^w$ are" should read -- where $x_i^w$, $y_i^w$ and $z_i^w$ are --.

Col. 6, line 23: " $\bar{x} = \frac{1}{n}\sum_{i=1}^{n} x_i^w, \bar{y} = \frac{1}{n}\sum_{i=1}^{n} y_i^w \text{ ja } \bar{z} = \frac{1}{n}\sum_{i=1}^{n} z_i^w$ " should read -- $\bar{x} = \frac{1}{n}\sum_{i=1}^{n} x_i^w, \bar{y} = \frac{1}{n}\sum_{i=1}^{n} y_i^w \text{ and } \bar{z} = \frac{1}{n}\sum_{i=1}^{n} z_i^w$ --

Col. 6, line 32-33: "samples $x_i^w$, $y_i^w$ ja $z_i^w$," should read -- samples $x_i^w$, $y_i^w$ and $z_i^w$, --.

Col. 6, line 35: "samples $x_i$, $y_1$ and $z_i$" should read -- samples $x_i$, $y_i$ and $z_i$ --.

Col. 7, line 2: "reverse sien functions" should read -- reverse sine functions --.

Col. 7, line 57: "positive or negative)," should read -- positive or negative, --.

Col. 9, line 58: "In block 432 is stored" should read -- In block 432 are stored --.

Column 14:
Claim 14, line 1: "if $sgn(\theta) < 0$, $sgn(\varphi) < 0$ and $sgn(\gamma) \geqq 0$" should be -- if $sgn(\theta) < 0$, $sgn(\varphi) < 0$ and $sgn(\gamma) < 0$ --.

Claim 14, line 17: "$Z_z = -z_c \sin|\gamma|$," should be -- $Z_z = z_c \sin|\gamma|$, --.

Column 15:
Claim 20, line 26: "$Y_c$" should be -- $y_c$ --.

UNITED STATES PATENT AND TRADEMARK OFFICE
CERTIFICATE OF CORRECTION

PATENT NO. : 6,983,219 B2
APPLICATION NO. : 10/186257
DATED : January 3, 2006
INVENTOR(S) : Mäntyjärvi et al.

It is certified that error appears in the above-identified patent and that said Letters Patent is hereby corrected as shown below:

Column 16:
Claim 22, line 8: "$Z_z = z_c \sin(\gamma)$," should be -- $Z_z = -z_c \sin(\gamma)$, --.

Signed and Sealed this

Fifth Day of December, 2006

JON W. DUDAS
*Director of the United States Patent and Trademark Office*